United States Patent [19]

Höffler et al.

[11] Patent Number: 5,043,357

[45] Date of Patent: Aug. 27, 1991

[54] VIRUCIDAL AGENT HAVING BROAD-SPECTRUM ACTIVITY

[75] Inventors: Jutta Höffler, Hamburg; Hans-J. Eggers, Köln, both of Fed. Rep. of Germany

[73] Assignee: Krüger GmbH & Co. KG, Bergisch Gladbach, Fed. Rep. of Germany

[21] Appl. No.: 443,037

[22] Filed: Dec. 4, 1989

Related U.S. Application Data

[63] Continuation of Ser. No. 43,469, Apr. 28, 1987, abandoned.

[30] Foreign Application Priority Data

Jul. 2, 1986 [DE] Fed. Rep. of Germany ....... 3622089

[51] Int. Cl.$^5$ .................. A61K 31/185; A61K 31/19; A61K 31/045; A61K 47/00
[52] U.S. Cl. .................................. 514/553; 514/557; 514/574; 514/724; 514/772; 514/783; 514/788

[58] Field of Search ................. 514/557, 724, 26, 784, 514/272, 783, 553, 574, 788

[56] References Cited

FOREIGN PATENT DOCUMENTS 3430709 3/1986 Fed. Rep. of Germany .
2103089 2/1983 United Kingdom .

OTHER PUBLICATIONS

Schwartz et al., "Surface Active Agents", Interscience Publishers Inc., 1949, Chapter 20, pp. 452-458.

Primary Examiner—Frederick E. Waddell
Assistant Examiner—Raymond J. Henley, III
Attorney, Agent, or Firm—Wegner, Cantor, Mueller & Player

[57] ABSTRACT

A virucidal agent having broad-spectrum activity contains at least 70% by weight of ethanol and/or propanols and from 0.5 to 5% by weight of a short-chain organic acid.

23 Claims, No Drawings

VIRUCIDAL AGENT HAVING BROAD-SPECTRUM ACTIVITY

This is a continuation of Ser. No. 07/043,469, filed Apr. 28, 1987 now abandoned.

The present invention relates to a virucidal agent having broad-spectrum activity and, more specifically, activity against various kinds of naked viruses, namely the virus strains poliovirus 1 (strain Mahoney), vacciniavirus (strain Elstree), SV 40-virus (e.g. strain 777) and adenovirus 2 (strain Adenoid 6) which virus strains are considered to be particularly dangerous.

BACKGROUND OF THE INVENTION

It has been known that viruses having a lipoid sheath are relatively sensitive and, thus, can be inactivated by virucidal disinfectants known so far. In contrast thereto, greater problems are caused by naked viruses, which are substantially more stable against conventional disinfectants and which can be inactivated only with relatively high concentrations of formaldehyde. However, formaldehyde is undesirable because of toxicity and does not allow the disinfection of contaminated parts of the body to be effected in either the clinic or the laboratory.

The literature on the disinfecting and inactivating activity of commercially available skin-compatible disinfectants is contradictory. Also the statements on the activities of alcohols are contradictory. Investigations on the activity of isopropanol against naked viruses, for example, have shown that this alcohol is only very weakly active or inactive. These investigations have further shown that ethanol and methanol are highly active if they contain less than 30 of water. Thus, German application OS 34 30 709 of Applicants shows a virucidal agent against naked viruses which consists of at least 70% of methanol and/or ethanol and from 1 to 10% of glycerol. This virucidal agent may additionally contain up to 5% of castor oil. Thorough investigations of these virucidal agents based on methanol and/or ethanol containing additives of glycerol and castor oil with a broad-spectrum of naked viruses, however, have resulted in the finding that these agents fail to be effective against certain kinds of problematic viruses, such as adenovirus 2 (strain Adenoid 6) and SV 40-virus (e.g. strain 777).

From German application OS 32 27 126 it is known that propagation of respiratory viruses can be interrupted or prevented by contacting the viruses with a short-chain organic acid. Citric acid, malic acid, succinic acid and benzoic acid as well as substituted derivatives thereof were mentioned as preferred organic acids. Furthermore it was indicated that the activity can be improved by surfactants, with the sodium salt of 1,4-bis(2-ethylhexyl)ester of sulfosuccinic acid and sodium dodecylsulfate being preferred. Said agents are active against the usual respiratory viruses such as rhinoviruses, parainfluenza viruses and adenoviruses. In prepared use these acids are applied, optionally together with the wetting agent, onto cellulose fabric or textiles. As further administration forms there have been mentioned nose sprays, face creams, hand lotions and lipsticks.

From the experimental results as set forth therein it is apparent that these acid-containing agents exhibited some activity also against adenovirus 5; however, in many cases a reduction by only two powers of ten or 99% was observed, and in part this was accomplished only after 5 minutes of action and/or at relatively high concentrations.

The Deutsche Vereinigung zur Bekämpfung von Viruskrankheiten (German Association for Combatting Virus Diseases) and the Bundesgesundheitsamt (Federal Health Office) are elaborating new regulations, according to which an agent may carry the designation virucidal agent only in the case that it is capable of inactivating the following four virus strains within a period of time which is appropriate for the intended use, e.g. for disinfecting a person's hands within from one to two minutes: poliovirus 1 (strain Mahoney), vacciniavirus (strain Elstree), SV 40-virus (e.g. strain 777) and adenovirus 2 (strain Adenoid 6). Thus, it is demanded that only those agents which have a broad-spectrum activity are allowed to be called virucidal agents.

SUMMARY OF THE INVENTION

It has now surprisingly been found that compositions containing at least 70% by weight of ethanol and/or propanols and from 1 to 5% by weight of a short-chain organic acid meet the above standards and, thus, are to be rated as virucidal agents having broad-spectrum activity.

These results are particularly unexpected because our own investigations using short-chain organic acids showed that these acids are nearly ineffective against, for example, poliovirus, so that the opinion of those skilled in the art was confirmed that most of the naked viruses are insensitive to acids. However, in the compositions of the invention there is a synergistic effect of the high percentage alcohol and the short-chain organic acid. Long-chain organic acids such as lauric acid no longer exhibit said effect. There is rather observed an effect similar to that shown upon the addition of triglycerides to pure alcohol according to the German Application OS 34 30 709. Also surprising was the finding that isopropanol alone, or in admixture with ethanol, upon the addition of the acids is highly active, whereas isopropanol by itself is inactive according to the German OS 34 30 709.

Thus, it has still not been elucidated wherein the activity of the respective alcohol and short-chain organic acid resides. Either of them alone is active only against some virus strains. In contrast thereto, the composition according to the invention is capable of sufficiently inactivating all of the strains of naked viruses rated to be problematic without undesirable effects.

Thus, subject matter of the present invention is a virucidal agent having broad-spectrum activity and containing at least 70% and up to 99.5% by weight of ethanol and/or propanols and from 0.5 to 5% by weight of a short-chain organic acid. Preferably, up to 5% by weight of a wetting agent is added to said virucidal agent. In order to render the new agents less irritating and better compatible to the skin, however without reducing the activity thereof, up to 5% of glycerol and up to 5% of castor oil may be added.

The short chain organic acids typically are two to six carbon acids. Preferred are mono-, di- and tricarboxylic acids of 2 to 4 carbon atoms which may be substituted by a hydroxy group. Examples are glycolic, citric, lactic, succinic and malic acid. Also suitable are sulfamic acids such as cyclamic acid.

A further subject matter of the present invention is the use of these compositions as virucidal agents.

The decision on whether to use ethanol, isopropanol or n-propanol or mixtures thereof depends on cost and on possible legal regulations relating to the commercial use of the alcohols. Thus, ethanol is more expensive and in many countries is subject to special legal provisions that may affect its use for the preparation of the agents according to the invention. The efficiency of ethanol is higher than that of isopropanol so that mixtures of the two alcohols may be desirable for reasons of cost and activity.

The agents of the invention are active to a degree such as to reduce the activity and infectivity of the virus strains rated as causing serious problems by at least 4 powers of ten within one to two minutes.

In the practical application, the agents of the invention may be used either as hand disinfectants, or they may be applied to the infected part of the skin by means of cotton, fabric pieces or similar auxiliaries. Due to the inactivating effect of triglycerides it is to be recommended in first application to remove skin fats and then to allow the agent of the invention produce its action in a second application. The glycerol or castor oil content prevents the skin from becoming dried to a high and undesirable degree and, thus, acts in a moisturizing manner. Moreover, it is possible after the use of the new virucidal agents to treat the skin with suitable skin care agents containing triglycerides, since the disinfection and inactivation has been effected in the absence of the triglycerides.

The composition and efficiency of the virucidal agents of the invention is apparent from the following examples and comparative experiments.

EXAMPLE 1

Two parts by weight of citric acid and 2 parts by weight of choline dodecylsulfonate are dissolved in 96 parts by weight of 80% ethanol. A part of this mixture was admixed with 1% of castor oil and 4% of glycerol.

EXAMPLE 2

Two parts by weight of glycolic acid are dissolved in 18 parts of water and 80 parts by weight of ethanol.

EXAMPLE 3

Two parts by weight of citric acid are dissolved in 28 parts by weight of water and 70 parts by weight of ethanol.

EXAMPLE 4

Two parts by weight of cyclohexanesulfamic acid are dissolved in 18 parts of water and 80 parts by weight of ethanol.

EXAMPLE 5

Two parts by weight of lactic acid are dissolved in 18 parts of water and 80 parts by weight of ethanol.

EXAMPLE 6

Two parts by weight of citric acid are dissolved in 18 parts by weight of water and 80 parts by weight of isopropanol.

The virus-inactivating effects of the compositions according to Examples 1 through 6 were tested with poliovirus type 1, strains Mahoney, in the presence of 10% fetal calf serum. The reduction in the virus titer (log 10, PBE/ml) was measured after periods of treatment of 1 minute and 2 minutes. It was found that in all cases the virus titer was lowered by more than 5 powers of ten. Only in Example 6 using isopropanol the virus titer was lowered merely by 4.9 powers of ten after 2 minutes.

For comparison, 80% ethanol, 70% ethanol, 2% aqueous glycolic acid and 2% aqueous citric acid were measured. The virus titer was lowered by about 2.5 powers of ten by the 80% ethanol, by about 1.2 powers of ten by the 70% ethanol and by a maximum of ½ power of ten by the aqueous acids.

The formulations of Examples 1 through 6 were further tested against vaccinia virus (strains Elstree), SV 40-virus (e.g. strain 777) and adenovirus 2 (strain Adenoid 6). It was shown that in all cases the virus titer was lowered by at least 4 powers of ten within 1 to 2 minutes. Ethanol or propanols alone did not exhibit sufficient activities against said viruses.

What is claimed is:

1. Virucidal agent containing 70 to 99.5% by weight of at least one member selected from the group consisting of ethanol, n-propanol and isopropanol, and from 0.5 to 5% by weight of a $C^2$-$C^6$-short-chain organic acid.

2. Virucidal agent of claim 1 wherein the organic acid is a $C^{2-4}$- mono-, di- or tricarboxylic acid optionally substituted by a hydroxy group.

3. Virucidal agent of claim 2, characterized in that the organic acid is at least one member selected from the group consisting of citric acid and glycolic acid.

4. The virucidal agent of claim 3, characterized in that it additionally contains up to 5% of glycerol and up to 5% of castor oil.

5. The virucidal agent of claim 2, characterized in that it additionally contains up to 5% of glycerol and up to 5% of castor oil.

6. Virucidal agent of claim 1 wherein the organic acid is cyclohexane-sulfamic acid.

7. The virucidal agent of claim 6, characterized in that it additionally contains up to 5% of glycerol and up to 5% of castor oil.

8. Virucidal agent of claim 1, characterized in that the organic acid is at least one member selected from the group consisting of citric acid and glycolic acid.

9. Virucidal agent of claim 1, characterized in that it contains choline dodecylsulfonate as a wetting agent.

10. The virucidal agent of claim 9, characterized in that it additionally contains up to 5% of glycerol and up to 5% of castor oil.

11. The virucidal agent of claim 1, characterized in that it additionally contains up to 5% of glycerol and up to 5% of castor oil.

12. The virucidal agent of claim 1, characterized in that it additionally contains up to 5% of glycerol and up to 5% of castor oil.

13. Virucidal agent of claim 1, wherein the organic acid is selected from the group consisting of glycolic acid, citric acid, lactic acid, succinic acid, malic acid and cyclohexanesulfamic acid.

14. Virucidal agent of claim 1, wherein the organic acid is selected from the group consisting of glycolic acid, citric acid, lactic acid, succinic acid and malic acid.

15. Virucidal agent of claim 1, wherein the organic acid is present at 0.5 to 2% by weight.

16. Virucidal agent of claim 1, wherein said at least one member selected from the group consisting of ethanol, n-propanol and isopropanol is present at 70 to 80% by weight.

17. Process of producing a topical virucidal effect on mammalian skin by applying a virucidally effective amount of an agent containing 70–99.5% by weight of at least one member selected from the group consisting of ethanol, n-propanol and isopropanol, and 0.5 to 5% by weight of a $C^{2-6}$ short-chain organic acid.

18. Process of claim 17, wherein the organic acid is selected from the group consisting of glycolic acid, citric acid, lactic acid, succinic acid, malic acid and cyclohexanesulfamic acid.

19. Process of claim 17 wherein the organic acid is a $C^{2-4}$-mono-, di- or tricarboxylic acid substituted by a hydroxy group.

20. Process of claim 17 wherein the organic acid is cyclohexanesulfamic acid.

21. Process of claim 17, wherein the organic acid is selected from the group consisting of glycolic acid, citric acid, lactic acid, succinic acid and malic acid.

22. Process of claim 17, wherein the organic acid is present at 0.5 to 2% by weight.

23. Process of claim 17, wherein said at least one member selected from the group consisting of ethanol, n-propanol and isopropanol is present at 70 to 80% by weight.

* * * * *